United States Patent
Hermosilla-Lara et al.

(10) Patent No.: US 8,248,065 B2
(45) Date of Patent: Aug. 21, 2012

(54) METHOD AND DEVICE FOR DETECTING STRUCTURAL ABNORMALITIES IN A SPHERICAL PARTICLE

(75) Inventors: Sébastien Hermosilla-Lara, Givry (FR); Lenaig Gravot, Longwy (FR)

(73) Assignee: Areva NP, Courbevoie (FR)

( * ) Notice: Subject to any disclaimer, the term of this patent is extended or adjusted under 35 U.S.C. 154(b) by 364 days.

(21) Appl. No.: 12/445,209

(22) PCT Filed: Oct. 11, 2007

(86) PCT No.: PCT/FR2007/001662
§ 371 (c)(1),
(2), (4) Date: Sep. 30, 2009

(87) PCT Pub. No.: WO2008/046986
PCT Pub. Date: Apr. 24, 2008

(65) Prior Publication Data
US 2010/0026325 A1 Feb. 4, 2010

(30) Foreign Application Priority Data
Oct. 13, 2006 (FR) .................................. 06 09018

(51) Int. Cl.
*G01N 27/82* (2006.01)
(52) U.S. Cl. ......... 324/240; 324/242; 324/238; 324/239
(58) Field of Classification Search ............... 324/242
See application file for complete search history.

(56) References Cited

U.S. PATENT DOCUMENTS

| | | | | |
|---|---|---|---|---|
| 4,659,989 A * | 4/1987 | Kerr | ................................ | 324/233 |
| 5,432,444 A * | 7/1995 | Yasohama et al. | ............ | 324/240 |
| 5,528,141 A * | 6/1996 | Kyriakis | ......................... | 324/230 |
| 5,969,528 A * | 10/1999 | Weaver | ........................... | 324/329 |
| 6,188,217 B1 * | 2/2001 | Linder | .......................... | 324/239 |
| 6,958,603 B2 * | 10/2005 | Kondo | ........................... | 324/239 |
| 7,355,395 B2 * | 4/2008 | Redko et al. | ................... | 324/240 |
| 2002/0067163 A1 * | 6/2002 | Goldberg et al. | ............. | 324/234 |

FOREIGN PATENT DOCUMENTS

| | | |
|---|---|---|
| FR | 2319115 A1 | 2/1977 |
| JP | 02136741 A | 5/1990 |
| WO | WO-02095766 A1 | 11/2002 |

OTHER PUBLICATIONS

McMaster et al., "Nondestructive Testing Handbook", 1986, 2nd Edition, vol. 4, pp. 195-198, American Society for Nondestructive Testing.

* cited by examiner

*Primary Examiner* — Richard Isla Rodas
(74) *Attorney, Agent, or Firm* — Connolly Bove Lodge & Hutz LLP

(57) ABSTRACT

The method for detecting at least one structural defect in a spherical particle (33) comprises at least the following steps of passing the particle (33) into at least one induction coil (15); exciting the induction coil (15) in order to induce Foucault currents in the particle (33); acquiring an output signal at the terminals of the induction coil (15); and analyzing the signal in order to establish whether or not the particle (33) comprises a structural defect. A plurality of output signals are acquired by passing the particle (33) successively into one or more induction coils (15) with different positions of the particle (33), the or each induction coil (15) being excited at least each time the particle (33) passes in order to induce Foucault currents in the particle (33).

13 Claims, 2 Drawing Sheets

METHOD AND DEVICE FOR DETECTING STRUCTURAL ABNORMALITIES IN A SPHERICAL PARTICLE

CROSS REFERENCE TO RELATED APPLICATIONS

Figure 1:
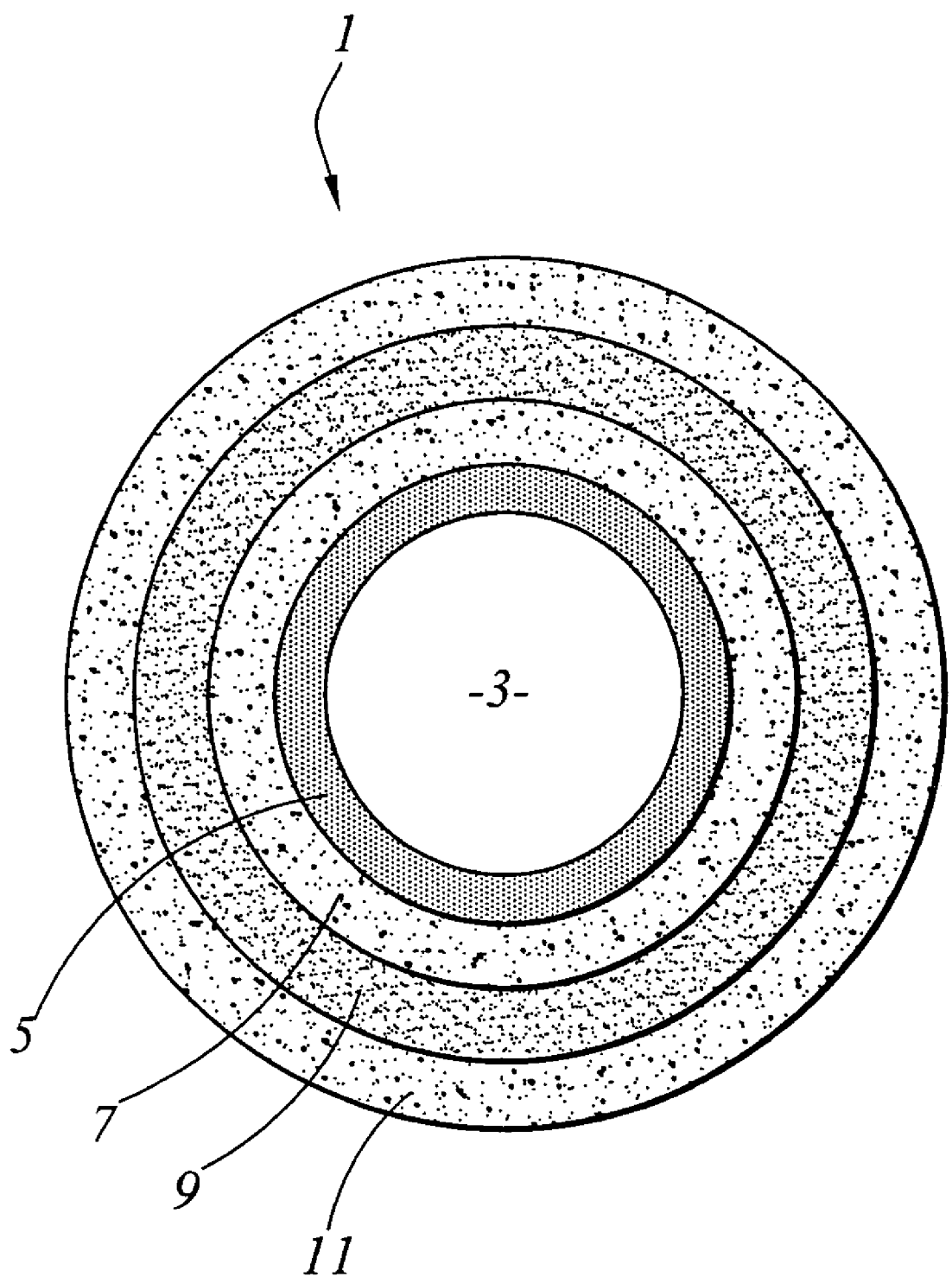

This application is a National Phase filing under 35 U.S.C. §371 of PCT/FR2007/001662 filed Oct. 11, 2007, which claims priority to Patent Application No. 0609018, filed in France on Oct. 13, 2006. The entire contents of each of the above-applications are incorporated herein by reference.

The invention generally relates to methods for detecting structural defects in a spherical particle, particularly in a nuclear fuel particle for high temperature or very high temperature reactors.

More specifically, the invention relates to, according to a first aspect, a method for detecting at least one structural defect in a spherical particle, of the type comprising at least the following steps of:
- passing the particle into at least one induction coil;
- exciting the induction coil in order to induce Foucault currents in the particle;
- acquiring an output signal at the terminals of the induction coil; and
- analysing the signal in order to establish whether or not the particle comprises a structural defect.

An article from the "Non-destructive testing handbook", second edition, volume 4, pages 195 to 197, ASNT, 1986, describes in a theoretical manner a method for detecting a fissure in a spherical particle by means of a circular induction coil. The article develops the theoretical aspects of such a detection method using Foucault currents and sets out the performance levels expected. It indicates that the output signal is a function of the position of the fissure in relation to the coil.

This method has the failing that the output signal acquired at the terminals of the induction coil is sensitive, not only to the presence and the orientation of the structural defect in the particle, but also to a number of other physical parameters of the particle, for example, its size, the material(s) constituting the particle, etc. Therefore, this method does not allow discrimination, with a high degree of reliability, between the non-defective particles and the particles comprising structural defects.

In this context, an object of the invention is to provide a method which is more reliable.

To that end, the invention relates to a detection method of the above-mentioned type, characterised in that a plurality of output signals are acquired by passing the particle successively into one or more induction coils with different positions of the particle, the or each induction coil being excited at least each time the particle passes in order to induce Foucault currents in the particle.

The method may also comprise one or more of the features below, considered individually or in accordance with any technically possible combination:
- the analysis step is carried out in accordance with a variable which represents the dispersion relative to each other of parameter values which are established from the output signals;
- the parameter is the impedance modulus of the induction coil which is excited when the particle is inside the induction coil;
- the variable which represents the dispersion is equal to the difference between the largest and the smallest of the established values of impedance moduli;
- the analysis step is carried out by comparing the variable which represents the dispersion with a predetermined threshold;
- the or each induction coil is excited by an electric current having a frequency which is between 30 and 50 MHz and preferably by an electric current having a frequency corresponding to the resonance frequency of the coil;
- the particle is displaced with a rotation movement whilst it successively passes through the induction coil(s);
- the particle successively passes through at least four different induction coils; and
- the particle is a nuclear fuel particle.

According to a second aspect, the invention relates to a device for carrying out the method above, the device comprising:
- a plurality of induction coils;
- means for passing the particle successively into the induction coils with different positions of the particle;
- means for exciting the induction coils in order to induce Foucault currents in the particle;
- means for acquiring an output signal at the terminals of each induction coil;
- means for analysing the output signals and establishing whether or not the particle comprises a structural defect.

The device may optionally comprise the following features:
- the induction coils are arranged vertically one above the other;
- the device comprises means for causing the particle to fall under gravity through the superimposed induction coils; and
- the means for causing the particle to fall under gravity through the superimposed induction coils comprise an inclined ramp which is capable of moving the particle substantially as far as a position perpendicularly above the coils.

Figure 2:
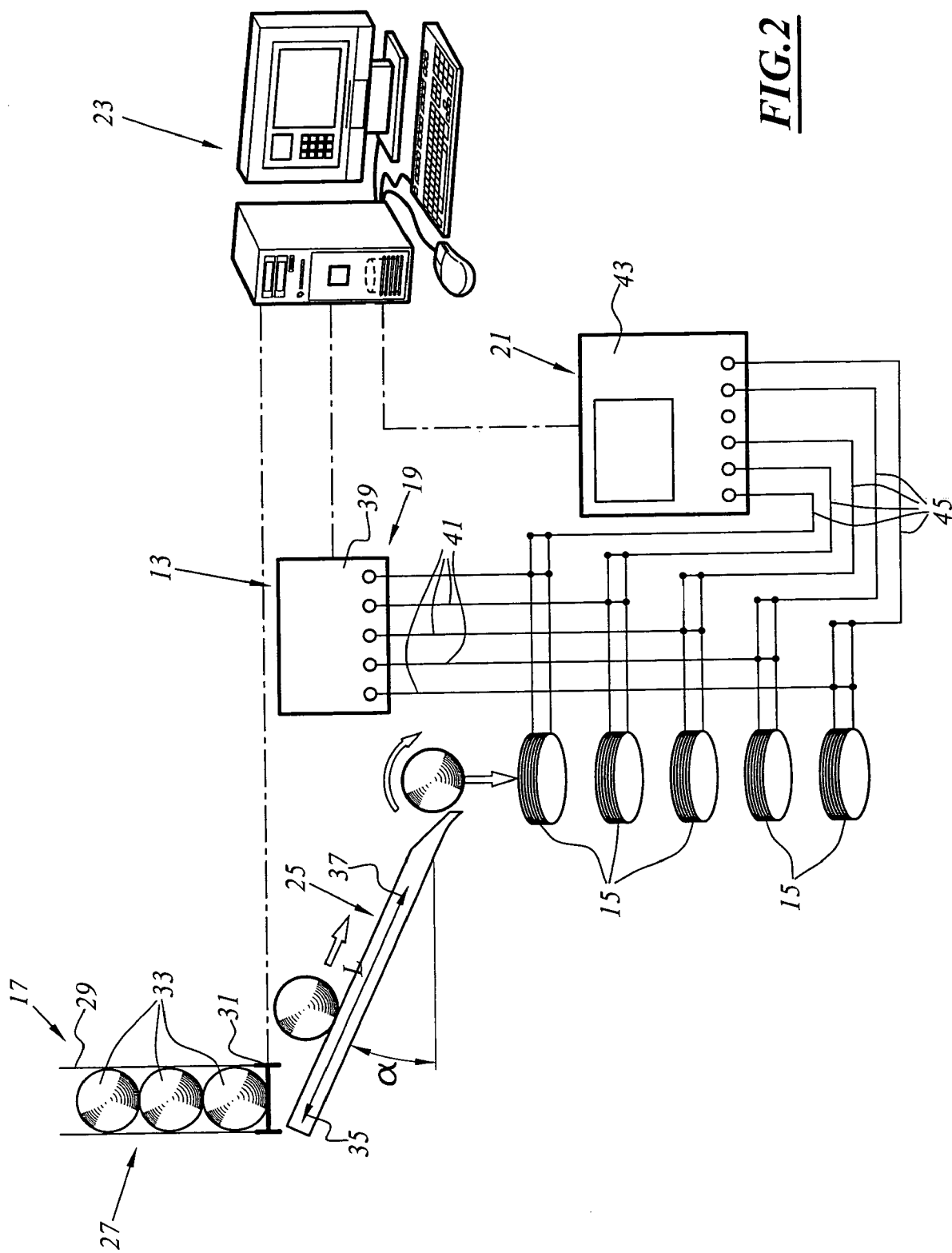

Other features and advantages of the invention will be appreciated from the following detailed description which is given by way of non-limiting example with reference to the appended Figures, in which:

FIG. 1 is a schematic equatorial section illustrating the structure of a nuclear fuel particle for a high temperature reactor; and FIG. 2 is a schematic view illustrating an installation for carrying out a detection method in accordance with the invention.

FIG. 1 schematically illustrates a nuclear fuel particle 1 for a high temperature or very high temperature reactor (HTR/VHTR).

In conventional manner, this particle 1 is generally of substantially spherical shape and comprises successively from the inner side towards the outer side:
- a fissile material core 3, for example, based on $UO_2$ or UCO,
- a layer 5 of porous pyrocarbon,
- a first layer 7 of dense pyrocarbon,
- a layer 9 of silicium carbide and
- a second layer 11 of dense pyrocarbon.

When such a particle is used, the porous pyrocarbon acts as a reservoir for the fission gases, the silicium carbide acts as a barrier against diffusion of the products of solid fission and the dense pyrocarbon ensures the mechanical resistance to the pressure of the fission gases.

The core 3 has, for example, a diameter of approximately 500 μm and the layers 5, 7, 9 and 11 have thicknesses of, for example, 95, 40, 35 and 40 μm, respectively.

It will be appreciated that the relative dimensions of the core 3 and the layers 5, 7, 9 and 11 have not been complied with in FIG. 1.

The layers, particularly the pyrocarbon layers 5, 7, 11, are deposited, for example, by a chemical vapour deposition method which is carried out in a fluidised bed furnace.

The device illustrated in FIG. 2 allows detection of any structural defects in one of the layers 5, 7, 9, 11 of the fuel particle of FIG. 1 or between the layers of the particle.

The structural defects which it is thereby possible to detect are as follows inter alia:
- losses of cohesion between layers, that is to say, the zones in which two superimposed layers are not in contact with each other but instead where a cavity exists between the two layers;
- fissures or cavities which are located inside the same layer;
- zones inside a layer in which the layer has defective porosity;
- zones in which a layer has a sphericity fault.

The detection device 13 comprises:
- five circular coils 15 for induction and measurement;
- means 17 for passing a particle to be tested successively into the induction coils 15;
- means 19 for exciting the induction coils 15 in order to induce Foucault currents in the particle to be tested;
- means 21 for acquiring an output signal at the terminals of each induction coil 15;
- analysis means 23 for establishing whether or not the particle comprises a structural defect in accordance with a variable which represents the dispersion relative to each other of parameter values which are established from the output signals.

In the example illustrated, the induction coils 15 are circular coils which are mutually identical. They are provided parallel with each other in a coaxial manner.

The induction coils 15 are arranged vertically one above the other. The vertical spacing between two coils is preferably between 8 and 40 mm in accordance with the operating frequency, the value of the current introduced and such that the coils are decoupled from each other. The vertical spacing between the coils becomes less as the operating frequency increases.

Each coil 15 comprises a number of turns which is between 5 and 35, preferably between 8 and 20. For example, each coil comprises 11 turns.

Each coil 15 has an inner diameter which is between 0.6 mm and 2 mm, preferably between 1 mm and 1.5 mm, depending on the diameter of the particle to be inspected. For example, the inner diameter of each coil is 1.2 mm. More specifically, each coil 15 generally comprises a hollow cylindrical tube of Pyrex® type glass, and a copper wire which is coiled on the outer surface of the glass tube. The particles to be tested pass inside the glass tube, the inner diameter of the tube being selected, for example, so as to be equal to the maximum diameter of the particles to be tested plus 0.2 mm. In this manner, a clearance of approximately 0.1 mm is left between the particle which passes through the glass tube and the internal surface of this tube.

Each coil 15 is constructed with a copper wire having a circular cross-section, having a diameter which is between 20 micrometers and 200 micrometers, preferably between 50 micrometers and 125 micrometers. The diameter of the wire is, for example, 100 micrometers.

The means 17 for moving the particle in the coils comprise, for example, an inclined ramp 25 and a charger 27 for storing the particles to be tested. The charger 27 comprises, for example, a cylindrical chute 29 having a vertical axis and means 31 for selectively blocking or disengaging a lower end of the chute 29. The particles 33 to be tested are stacked vertically in the chute 29. The chute 29 is located perpendicularly above an upper end 35 of the inclined ramp 25.

The inclined ramp 25 further has a lower end 37 which is located above the coils 15, substantially vertically thereabove. The inclined ramp 25 has, between its ends 35 and 37, a length L which is several tens of centimeters. The ramp 25 forms, relative to the horizontal, an angle α which is between 20° and 45°.

The means 19 for exciting the induction coils comprise an alternating current source 39 and electrical conductors 41 which connect the current source 39 to the terminals of each of the coils 15. The current source 39 comprises means for adjusting the frequency of the excitation current transmitted to each of the coils 15. The frequency of the excitation current is between 30 MHz and 50 MHz, preferably between 30 MHz and 35 MHz. For example, the frequency of the excitation current is 32 MHz and is equal to the resonance frequency of the coils.

The excitation current is identical for each of the coils 15. In a variant, the excitation current may be different for each of the coils 15, in particular the frequency thereof.

The means 21 for acquiring an output signal at the terminals of each coil 15 comprise a multi-channel impedance meter 43 and electrical conductors 45 which connect the terminals of each coil 15 to one of the channels of the impedance meter 43. The output signal acquired at the terminals of each of the induction coils 15 is an electric current, from which the impedance meter 43 establishes the impedance modulus of the excited induction coil 15 when the particle is inside the induction coil.

The analysis means 23 comprise data-processing calculation means which are connected to the impedance meter 43. The values of the impedance modulus of each induction coil 15 which are established by the impedance meter 43 are transmitted thereby to the data-processing means 23.

The data-processing means 23 further control the current source 39 and the means 31 which allow the chute 29 to be blocked or disengaged.

There will now be described in detail the method which allows detection of the structural defects in a fuel particle by means of the device of FIG. 2.

Firstly, the data-processing means 23 instruct the means 31 to disengage the lower end of the chute 29 so as to allow a particle 33 to fall onto the inclined ramp 25. Once the particle 33 has passed, the means 31 again block the chute 29.

The particle 33 falls onto the upper end 35 of the inclined ramp and travels along the inclined ramp 25 as far as the lower end 37 thereof. Subsequently, it falls, under the effect of gravity, through the various superimposed coils 15. The lower end 37 of the inclined ramp is positioned in such a manner that the particle 33 falls substantially vertically in accordance with the axis of the various coils 15.

The particle 33 is displaced with a movement involving rotation about itself while it passes successively through the induction coils 15 because it has traveled along the inclined ramp 25. The vertical translation speed and the rotation speed of the particle 33 are a function of the length L of the inclined ramp 25 and the angle of inclination α thereof. Those parameters are adjusted in accordance with the vertical spacing between the coils 15 and in accordance with the size of the particle to be tested.

The data-processing means 23 instruct the current generator 39 to pass an excitation current into the coils 15. Preferably, the frequency of the excitation current is selected so as to correspond substantially to the resonance frequency of the coils. The current generator 39 supplies the induction coils 15, preferably permanently, during the series of operations for controlling an entire batch of particles 33.

Each induction coil 15, when the particle 33 passes through it, induces Foucault currents in the particle. Those Foucault currents in turn produce an induced magnetic field which disrupts the excitation current.

In particular, the induced magnetic field modifies the impedance of the induction coil 15 which is excited when the particle passes.

The impedance meter 43 permanently examines the impedance at the terminals of the different coils 15 and establishes the impedance of each of the induction coils 15 when the particle is inside the induction coil. The passage time of the particle can readily be fixed because it corresponds to an abrupt variation in the impedance of the induction coil 15. The impedance meter 43 transmits the impedance modulus established to the data-processing means 23.

The data-processing means 23 receive the five impedance moduli of the induction coils 15 which are excited when the particle is inside those coils. The means 23 calculate a variable which represents the dispersion of the impedance moduli which are established relative to each other. The variable which represents the dispersion of the impedance moduli relative to each other is equal to the difference between the largest of the impedance moduli established and the smallest of the impedance moduli established.

The means 23 subsequently compare the calculated variable which represents the dispersion with a predetermined threshold. If the representative variable is greater than the predetermined threshold, the particle is considered to have a structural defect. If the representative variable is less than the predetermined threshold, the particle is considered to be non-defective, that is to say, not to have any structural defect.

If the particle comprises a structural defect, the impedance moduli of the various induction coils will be very different from each other because the particle rotates whilst passing through the various coils and does not occupy the same relative position in relation to each of them when it passes through it. Therefore, the structural defect does not occupy the same position when it passes into the various coils 15 and, consequently, the impedance moduli established will have a great dispersion in that instance.

Conversely, if the particle does not have any structural defect, the rotation of the particle about itself will not significantly change the impedance moduli of the various coils 15. The dispersion of the impedance moduli will therefore be small.

The method described above has a number of advantages.

The fact that a plurality of output signals are acquired for different positions of the particle allows discrimination between non-defective particles and particles having a structural defect to be carried out in a very reliable manner.

The reliability is further increased because the analysis step, during which it is determined whether or not the particle comprises a structural defect, is carried out in accordance with a variable which represents the dispersion relative to each other of parameter values which are established from the output signals.

The dispersion of the output signals relative to each other is sensitive practically only to the presence of structural defects in the particle. This dispersion is almost insensitive to the other physical parameters of the particle.

The criterion selected in order to establish whether or not the particle is non-defective is particularly simple because the calculated dispersion is compared with a simple predetermined threshold.

The method allows testing of the particles at a particularly high rate because the physical phenomena involving electromagnetic diffusion are extremely rapid and, on the other hand, the processing of the output signals acquired requires a low number of calculations.

The use of means such as an inclined ramp in order to rotate the particle to be tested ensures that a great dispersion is obtained in the output signals when the particle comprises a structural defect.

Working with excitation currents at the resonance frequency of the coils allows acquisition of the output signals having a higher magnitude and therefore facilitates the processing of the signals acquired.

The method and the device described above may have a number of variants.

The particle may travel into more or less than five induction coils. It may, for example, travel into only four induction coils or, instead, travel into a high number of coils, for example, twenty or thirty induction coils which are arranged one above the other.

When a large number of induction coils are used and therefore a large number of output signals are provided (for example, twenty or thirty), it is possible to evaluate the dispersion of the output signals relative to each other, not by calculating the difference between the highest signal and the lowest signal, but instead by using the standard deviation of this group of output signals.

The current source 39 may not be separate from the impedance meter but instead may be integrated in the impedance meter.

According to another embodiment of the invention, it is possible to carry out the method in a device comprising a single induction coil, and mechanical means for passing the particle to be tested through the single coil successively several times. For example, the coil is enclosed in an oscillating tube. It is provided at the centre of the tube and the particle to be tested is provided inside the tube. When the tube is inclined at a first side in such a manner that a first end of the tube is lower and a second end of the tube is higher, the sphere travels over the base of the tube as far as the first end and passes through the coil. Subsequently, when the tube tilts in the opposite direction, in such a manner that the second end is lower and the first end is higher, the particle travels in the opposite direction along the tube as far as the second end and again passes through the coil. In this manner, a plurality of tilting actions of the tube are carried out, with an output signal being collected each time the particle passes through the coil. The output signals are processed as explained above.

The means for moving the particle in order to have output signals for different relative positions of the particle may not be an inclined ramp, but instead may comprise any other means for rotating the particle.

The means 27 for causing the particles to be tested to fall onto the inclined ramp 25 may be different from those described above. The chute 29 may be, for example, horizontal and not vertical. Any other mechanical means for depositing the particles to be tested one by one onto the ramp 25 may be used.

Furthermore, the detection device may comprise a bent guiding piece or a deflector which is capable of orientating the particles 33 which leave the lower end 37 of the inclined ramp in accordance with a vertical trajectory along the axis of the coils 15.

It is also possible to use, in place of the multi-channel impedance meter, a plurality of impedance meters which are each dedicated to an induction coil and which communicate the impedance measured at the terminals of the coil to the data-processing means.

The method and the device are suitable for controlling the particles of all types of high temperature reactor, for example, types known under the acronyms HTR (High Temperature Reactor), HTTR (High Temperature engineering Test Reactor), VHTR (Very High Temperature Reactor), THTR (Thorium High Temperature Reactor), GT-MHR (Gas Turbine Modular Helium Reactor), MHTGR (Modular High Temperature Gas Reactor), HTGR (High Temperature Gas cooled Reactor) and PBMR (Pebble Bed Modular Reactor). They are also suitable for controlling all types of spherical particle comprising a layer of electrically conductive material.

The invention claimed is:

1. A method for detecting at least one structural defect in a spherical particle, the method comprising at least the following steps of:
    passing the particle into at least two induction coils;
    exciting the induction coils in order to induce Foucault currents in the particle;
    acquiring an output signal at the terminals of the induction coils; and
    analyzing the signal in order to establish whether or not the particle comprises a structural defect;
    wherein a plurality of output signals are acquired by passing the particle successively into the induction coils so that the particle exhibits a different rotational position with respect to its center as it passes through each induction coil, each induction coil being excited at least each time the particle passes in order to induce Foucault currents in the particle, the presence of a structural defect in the particle being established from the signals acquired.

2. The method according to claim 1, wherein the analysis step is carried out in accordance with a variable which represents the dispersion relative to each other of parameter values which are established from the output signals.

3. The method according to claim 2, wherein the parameter is the impedance modulus of the respective induction coil which is excited when the particle is inside the induction coil.

4. The method according to claim 3, wherein the variable which represents the dispersion is equal to the difference between the largest and the smallest of the established values of impedance moduli.

5. The method according to claim 1, wherein the analysis step is carried out by comparing the variable which represents the dispersion with a predetermined threshold.

6. The method according to claim 1, wherein each induction coil is excited by an electric current having a frequency which is between 30 and 50 MHz.

7. The method according to claim 1, wherein each coil is excited by an electric current having a frequency corresponding to a resonance frequency of the coil.

8. The method according to claim 1, wherein the particle successively passes through at least four different induction coils.

9. The method according to claim 1, wherein the particle is a nuclear fuel particle.

10. A device for carrying out the method for detecting at least one structural defect in a spherical particle according to claim 1, the device comprising:
    a plurality of induction coils;
    means for passing the particle successively into the induction coils so that the particle exhibits a different rotational position with respect to its center as it passes through each induction coil;
    means for exciting the induction coils in order to induce Foucault currents in the particle;
    means for acquiring an output signal at the terminals of each induction coil;
    means for analyzing the output signals and establishing whether or not the particle comprises a structural defect.

11. The device according to claim 10, wherein the induction coils are arranged vertically one above the other.

12. The device according to claim 11, wherein it comprises means for causing the particle to fall under gravity through the superimposed induction coils.

13. The device according to claim 12, wherein the means for causing the particle to fall under gravity through the superimposed induction coils comprise an inclined ramp which is capable of moving the particle substantially as far as a position perpendicularly above the coils.

* * * * *